United States Patent [19]

Kasan et al.

[11] Patent Number: 4,883,805

[45] Date of Patent: Nov. 28, 1989

[54] STABLE, INJECTABLE SOLUTIONS OF VINCA DIMER SALTS

[75] Inventors: Rodney Kasan, Raanana; Haim Yellin, Ramat-Gan; Michael Seiffe, Raanana, all of Israel

[73] Assignee: Teva Pharmaceutical Industries Ltd., Israel

[21] Appl. No.: 78,805

[22] Filed: Jul. 28, 1987

[30] Foreign Application Priority Data

Jul. 6, 1987 [IL] Israel ........................................ 83086

[51] Int. Cl.⁴ ............................................ A61K 31/435
[52] U.S. Cl. .................... 514/411; 514/283; 514/408; 514/410; 514/427; 514/579; 514/740; 562/566
[58] Field of Search ................. 562/565, 566; 514/281, 514/283, 408, 410, 411, 427, 579, 740, 280

[56] References Cited

U.S. PATENT DOCUMENTS 4,619,935 10/1986 Robinson ............................ 514/281
4,707,498 11/1987 Kolb .................................... 514/671
4,708,962 11/1987 Higa .................................... 514/475

*Primary Examiner*—William R. Dixon, Jr.
*Assistant Examiner*—James M. Hunter
*Attorney, Agent, or Firm*—Steinberg & Raskin

[57] ABSTRACT

A stable, injectable pharmaceutical composition of vinca dimer salts. The compositions are in the form of an aqueous solution comprising per 1 ml of solution:

from about 0.2 to about 2 mg of one or more pharmaceutically acceptable vinca dimer salts;

from about 0.1 to about 1.0 mg of a pharmaceutically acceptable ethylenediamine-tetraacetic acid (EDTA) salt;

acetate buffer in an amount necessary to maintain said aqueous solution at a pH of from about 3.0 to about 5.5; and from about 1.5 to about 2.5 mg of a preservative selected from methyl paraben, propyl paraben and mixtures thereof.

15 Claims, No Drawings

STABLE, INJECTABLE SOLUTIONS OF VINCA DIMER SALTS

BACKGROUND OF THE INVENTION

This invention provides a stable, injectable aqueous solution of vinca dimer salts, suitable for intravenuous injection for the treatment of neoplastic diseases, particularly leukemias, in humans.

Certain vinca alkaloids, being dimeric indole-dihydroindole compounds, have been used for some time in chemotherapy as oncolytic drugs, particularly for the treatment of leukemias. Among those so-called vinca dimers, there might be mentioned especially vincristine, vinblastine and vindesine (an amide derivative of vinblastine). The treatment consists of intravenous administration of pharmaceutically acceptable salts of the vinca dimers, in most cases the sulfate salt, to patients suffering from neoplastic diseases. Owing to the toxic properties of the vinca dimer salts, these must be administered in carefully accurate dosages.

In past years, vinca dimer salts for chemotherapy, and particularly vincristine sulfate, were marketed in sealed vials containing a desired dosage of lyophilized vinca dimer salt, from which an aqueous solution for injection had to be reconsituted in situ. Such a procedure involves many drawbacks as compared to the use of ready made injectable solutions, the main drawbacks being: errors in concentration of the vinca dimer salt owing to improper reconsitution of the lyophilized product; risk of contact with the toxic drug to the medical personnel preparing the injectable solutions; and waste of these very expensive drugs resulting from the need to discard the excesses of such reconstituted injectable solutions, which can be stored for comparatively short periods only (the recommended life of a reconsituted vincristine sulfate solution is 14 days at refrigerator temperatures, whereafter the solution becomes hazy and a precipitate forms therein).

Stable, ready-to-use aqueous solutions of vinca dimer salts were disclosed in Israel Patent Specification No. 69203 to Eli Lilly & Company and in the corresponding U.S. Pat. No. 4,619,935. In accordance with said Israel Patent the formulation comprises, in addition to a pharmaceutically acceptable vinca dimer salt, a polyol, an acetate buffer to maintain the pH of the solution between 3.0 and 5.0 and a preservative. As contrasted thereto, the U.S. Pat. No. 4,619,935 is restricted to formulations comprising an aqueous solution of about 1-2 mg/ml of a vincristine salt, about 10-100 mg/ml of a polyol selected from mannitol, sorbitol and sucrose, an acetate buffer as in the corresponding Israel patent and about 1-2 mg/ml of a preservative selected from methyl paraben and propyl paraben, singly or in combination. The formulations of this U.S. patent thus roughly correspond to the preferred embodiments described and claimed in Israel patent No. 69203. Both said Israel and U.S. patents state (in Example 4 therein) that the vincristine sulfate formulations disclosed therein "have remained physically and chemically acceptable for pharmaceutical use for periods up to 1 year at 5° C.". However, the stability test results given in the same Example 4 of these patents merely showed that said formulations "maintained 94–99% of their initial concentration after storage at 5° C. for about 9 months".

SUMMARY OF THE INVENTION

It is the object of the present invention to provide injectable aqueous solutions of vinca dimer salts having a significantly increased storage stability, as compared to the aforementioned known solutions.

The above object is achieved by the present invention as a consequence of the totally unexpected and surprising finding, that when about 0.1-1.0 mg/ml of a salt of ethylenediamine-tetraacetic acid (also referred to as "Edetate salt" and hereinafter as "EDTA-salt") is added to aqueous solutions of vinca dimer salts, comprising the conventional acetate buffer system and conventional preservatives (but no polyol as required in the aforementioned Israel patent No. 69203 and U.S. Pat. No. 4,619,935), the solutions remain stable for about 20 months, and even up to 30 months, at temperatures of 2–8° C., according to the accepted stability specifications (i.e. 90–110% of the labeled amount of the vinca dimer salt component). Furthermore, aqueous vincristine sulfate solutions in accordance with the present invention were found to be stable for up to 9 months even at room temperature.

The invention thus provides a stable, injectable pharmaceutical composition consisting in the form of an aqueous solution comprising per 1 ml of solution:

from about 0.2 to about 2 mg of one or more pharmaceutically acceptable vinca dimer salts;

from about 0.1 to about 1.0 mg of a pharmaceutically acceptable ethylenediamine-tetraacetic acid (EDTA) salt;

acetate buffer in an amount necessary to maintain said aqueous solution at a pH of from about 3.0 to about 5.5; and from about 1.5 to about 2.5 mg of a preservative selected from methyl paraben, propyl paraben and mixtures thereof.

The above formulation is applicable to any of the conventional oncolytic drugs consisting of vinca dimer salts, particularly salts of vincristine, vinblastine and vindesine, and the present invention is not restricted to vincristine sulfate solutions which are described in detail in the Examples herein, by way of non-limiting example only. Similarly, the present invention is not limited to the sulfate salts of the vinca dimers, although these are usually the preferred ones, and any other pharmaceutically acceptable salt may be used.

DESCRIPTION OF THE PREFERRED EMBODIMENTS

The vinca dimer salts are present in the injectable aqueous solutions according to the invention at concentrations of from about 0.2 to about 2 mg/ml as stated above, preferably from about 0.5 to about 1 mg/ml. For commercial reasons concentrations of about 0.5 and about 1.0 mg/ml of these salts are the most preferred ones.

The EDTA salts which may be used in accordance with the present invention are illustrated in the following non-limiting examples by the ethylenediaminetetraacetic acid disodium salt (EDTA-$Na_2$) but the invention is in no way restricted thereto and any other pharmaceutically acceptable EDTA salt, such as the dipotassium salt, can be used.

As stated above the injectable solutions according to the present invention are maintained at a pH of about 3.0–5.5, preferably about 4.0–5.0, by means of an acetate buffer system. A suitable such buffer system consists of about 1.0 mg/ml of sodium acetate (trihydrate) in combination with about 0.005 ml/ml of a 10% v/v aqueous acetic acid solution. For vincristine sulfate solutions, a pH of 4.5 is most preferred.

The preservatives included in the injectable solutions of the vinca dimer salts in accordance with the present invention, namely methyl paraben and propyl paraben (i.e. methyl and propyl hydroxybenzoates, respectively) and combinations thereof, have been found to be most suitable for preserving such solutions. The total concentration of the methyl and/or propyl paraben in the solutions according to the invention will generally be between about 1.5 to about 2.5 mg/ml, preferably about 2.0 mg/ml. A particularly preferred combination is 1.8 mg/ml of methyl paraben and 0.2 mg/ml of propyl paraben.

It has been found in accordance with the present invention that solutions of vinca dimer salts including 1.8 mg/ml of methyl paraben and 0.2 mg/ml of propyl paraben generally retained more than 90% of the total initial concentration of parabens after 20 months of storage at 2°–8° C. and even after storage at room temperatures for the same length of time.

The pharmaceutical composition according to the present invention, is preferably in the form of an aqueous solution comprising per 1 ml of solution;
from about 0.5 to about 1 mg of vincristine sulfate;
from about 0.25 to about 0.75 mg of EDTA-disodium salt (EDTA-Na$_2$);
acetate buffer in an amount sufficient to maintain a pH from about 4.0 to about 5.0 in the solution; and
about 2.0 mg of a preservative selective from methyl paraben, propyl paraben and mixtures thereof. The pH is preferably about 4.5, while the pharmaceutical more preferably comprises per 1 ml of solution;
about 1.0 mg of vincristine sulfate;
about 1.8 mg of methyl paraben;
about 0.2 mg of propyl paraben;
about 0.5 mg of EDTA-Na$_2$;
about 1.0 mg of sodium acetate (trihydrate); and
about 0.005 ml of a 10 percent v/v aqueous acetic acid solution.

Alternatively, the pharmaceutical composition according to the present invention is more preferably in the form of an aqueous solution comprising per 1 ml of solution;
about 0.5 mg of vincristine sulfate;
about 1.8 mg of methyl paraben;
about 0.2 mg of propyl paraben;
about 0.5 mg of EDTA-Na$_2$;
about 1.0 mg of sodium acetate (trihydrate); and
about 0.005 ml of 10% v/v aqueous acetic acid solution.

The invention will now be described in more detail, by way of illustration only, in the following non-limiting examples:

EXAMPLE 1

A stable injectable aqueous solution containing 0.5 mg/ml of vincristine sulfate is prepared as follows:

| Materials | |
| --- | --- |
| Vincristine sulfate BP/USP | Plantex, Israel |
| Methyl hydroxybenzoate BP/NF (methyl paraben) | Machteshim, Israel |
| Propyl hydroxybenzoate BP/NF (propyl paraben) | Machteshim, Israel |
| Edetate disodium BP/USP | Merck, Germany |
| Sodium Acetate 3H$_2$O BP/USP | Merck, Germany |

| Materials | |
| --- | --- |
| Acetic acid BP/NF | Merck, Germany |

Procedure

The work was carried out in a sterile laboratory and an inert atmosphere (nitrogen) was kept throughout the manufacturing procedure.

0.5 g of EDTA-Na$_2$, 1.8 g of methyl paraben and 0.2 g of propyl paraben were dissolved in boiling, deaerated water. The solution was cooled to room temperature and 1.0 g of sodium acetate trihydrate and 0.005 ml of an aqueous 10% v/v acetic acid solution were added. The resulting solution was cooled to 2–8° C. and 0.5 g of vincristine sulfate were dissolved therein. The solution was then brought to a final volume of 1 liter with deaerated water and filtered through a 0.2 um filter.

1 ml portions of the solution were filled into glass vials (Amber BP/USP Type I) which were sealed under an inert nitrogen atmosphere.

EXAMPLE 2

A stable aqueous vincristine sulfate solution containing about 1 mg/ml of vincristine sulfate was prepared by the procedure of Example 1, except that 1.0 g of vincristine sulfate was used instead of 0.5 g.

EXAMPLE 3

Amber glass vials containing 2, 4 or 10 ml of a 0.5 mg/ml vincristine sulfate solution prepared in accordance with Example 1 and similar vials containing 1.2 or 5 ml of a 1 mg/ml solution of vincristine sulfate prepared in accordance with Example 2, were stored in the dark for periods up to 20 months at a temperature of 2–8° C. and up to 9 months at room temperatures.

The results are summarized in the following Tables I and II as % of the initial vincristine sulfate concentration. Each of the values in Tables I and II is the mean of the values obtained from duplicate samples analyzed in accordance with the SI-10115 assay method (by HPLC; for validation of this method cf. SI24506).

TABLE I

Stability of Vincristine Sulfate Solutions
After Storage for 20 Months at 2–8° C.
Assayed Concentration of Vincristine Sulfate
as % of Initial Concentration
(mean of 2 assays)*

| Initial Concentration 0.5 mg/ml | Initial Concentration 1.0 mg/ml |
| --- | --- |
| 99.7 | 102.2 |
| 99.3 | 90.7 |
| 97.9 | 97.7 |
| 94.5 | 104.7 |
| 90.5 | 103.6 |
| 96.7 | 96.7 |
| 98.6 | 97.6 |
| 94.9 | 103.2 |
| 99.5 | |

*vials were stored in inverted position

TABLE II

Stability of Vincristine Sulfate Solutions
After Storage for 9 Months at Room Temperature
Assayed Concentration of Vincristine Sulfate
as % of Initial Concentration
(mean of 2 assays)*

| Initial Concentration 0.5 mg/ml | Initial Concentration 1.0 mg/ml |
| --- | --- |
| 96.1 | 97.6 |
| 93.5 | 98.3 |
| 90.0 | 98.1 |
| 91.8 | 93.7 |
| 90.5 | 96.6 |
| 91.1 | 99.7 |
| 90.2 | 93.6 |
| 93.1 | 93.2 |
|  | 92.1 |

*vials were stored in inverted position

We claim:

1. A stable, injectable pharmaceutical composition comprising an aqueous solution comprising per 1 ml of solution:
   from about 0.2 to about 2 mg of one or more pharmaceutically acceptable vinca dimer salts;
   from about 0.1 to about 1.0 mg of a pharmaceutically acceptable ethylenediamine-tetraacetic acid (EDTA) salt;
   acetate buffer in an amount necessary to maintain said aqueous solution at a pH of from about 3.0 to about 5.5; and
   from about 1.5 to about 2.5 mg of a preservative selected from methyl paraben, propyl paraben and mixtures thereof.

2. A pharmaceutical composition according to claim 1, wherein said vinca dimer salt is vincristine sulfate.

3. A pharmaceutical composition according to claim 2, wherein said aqueous solution comprises per 1 ml.
   from about 0.5 to about 1 mg of vincristine sulfate;
   from about 0.25 to about 0.75 mg of EDTA-disodium salt (EDTA-Na2);
   acetate buffer in an amount sufficient to maintain a pH of from about 4.0 to about 5.0 in the solution; and
   about 2.0 mg of a preservative selected from methyl paraben, propyl paraben and mixtures thereof.

4. A pharmaceutical composition according to claim 3, wherein the pH is about 4.5.

5. A pharmaceutical composition according to claim 3 wherein said aqueous solution comprises per 1 ml;
   about 1.0 mg of vincristine sulfate;
   about 1.8 mg of methyl paraben;
   about 0.2 mg of propyl paraben;
   about 0.5 mg of EDTA-Na$_2$;
   about 1.0 mg of sodium acetate (trihydrate); and
   about 0.005 ml of a 10% v/v aqueous acetic acid solution.

6. A pharmaceutical composition according to claim 3, wherein said aqueous solution comprises per 1 ml:
   about 0.5 mg of vincristine sulfate;
   about 1.8 mg of methyl paraben;
   about 0.2 mg of propyl paraben;
   about 0.5 mg of EDTA-Na$_2$;
   about 1.0 mg of sodium acetate (trihydrate); and
   about 0.005 ml of a 10% v/v aqueous acetic acid solution.

7. The composition of claim 1, wherein said vinca dimer salt is selected from salts of vincristine, vinblastine, and vindesine.

8. The composition of claim 1, comprising about 0.5 to about 1 mg/ml of said vinca dimer salt.

9. The composition of claim 1, wherein said EDTA salt is disodium salt of EDTA (EDTA-Na$_2$).

10. The composition of claim 1, wherein said acetate buffer is present in an amount maintaining said solution at a pH of about 4.0–5.0.

11. The composition of claim 1, wherein said acetate buffer comprises about 1.0 mg/ml sodium acetate (trihydrate in combination with about 0.005 ml/mg of a 10% v/v aqueous acetic acid solution.

12. The composition of claim 1, wherein said preservative is present in a concentration of about 2.0 mg/ml.

13. The composition of claim 12, wherein said preservative comprises about 1.8 mg/ml methyl paraben and about 0.2 mg/ml propyl paraben.

14. The composition of claim 1, wherein said aqueous solution remains stable for at least about 20 months at temperatures of 2°–8° C.

15. The composition of claim 14, wherein said solution retains at least about 90% of total initial concentration of said preservative after about 20 months at temperatures of 2°–8° C.

* * * * *